United States Patent [19]

Young

[11] 4,365,084

[45] Dec. 21, 1982

[54] PREPARATION OF ALKYL CARBOXYLATES

[75] Inventor: Lewis B. Young, Skillman, N.J.

[73] Assignee: Mobil Oil Corporation, New York, N.Y.

[21] Appl. No.: 218,148

[22] Filed: Dec. 19, 1980

[51] Int. Cl.$^3$ ............................................. C07C 67/04
[52] U.S. Cl. .............................. 560/247; 260/410.9 R; 560/103; 560/106; 560/226; 560/227; 560/241
[58] Field of Search ............... 560/247, 241, 103, 226, 560/106; 260/410.9 R

[56] References Cited

U.S. PATENT DOCUMENTS

| | | | |
|---|---|---|---|
| 3,014,066 | 12/1961 | Kerr ................................... | 560/247 |
| 3,085,108 | 4/1963 | Stepanek ............................ | 560/247 |
| 3,096,365 | 7/1963 | Heislor ............................... | 560/247 |
| 3,492,341 | 1/1970 | Trevillyan .......................... | 560/247 |

Primary Examiner—Michael L. Shippen
Attorney, Agent, or Firm—Charles A. Huggett; Michael G. Gilman; George W. Allen

[57] ABSTRACT

A method for preparation of alkyl carboxylate compounds, and especially α-methylalkyl carboxylate compounds, by reaction of an olefin and a carboxylic acid compound in the presence of a particular type of zeolite catalyst. The zeolites are characterized by a silica to alumina mole ratio of at least 12 and a constraint index of 1 to 12. Zeolites ZSM-5 and ZSM-12 are particularly preferred.

12 Claims, No Drawings

PREPARATION OF ALKYL CARBOXYLATES

BACKGROUND OF THE INVENTION

1. Field of the Invention

This invention is concerned with a novel method for preparation of alkylcarboxylates, and particularly α-methylalkyl carboxylates, by reaction of carboxylic acids with olefinic compounds in the presence of a particular type of crystalline zeolite catalyst.

2. Description of the Prior Art

The addition of carboxylic acids to olefins to make esters is known. The chemical literature describes the use of Lewis acid catalysts, such as $BF_3$, to promote the reaction. However, particularly in the case of internal olefins, the reaction will result in addition of the carboxylic acid to both ends of the double bond, thereby giving rise to a mixture of carboxylate products. Mineral acids (e.g., $H_2SO_4$) are also reported to catalyze the reaction, but the result is much the same, i.e., non-selective addition of the carboxylic acid to either side of the carbon-carbon double bond.

In the past, the only known reaction route to produce α-methylalkyl carboxylates directly has required the utilization of expensive alpha-olefins. Reaction with internal or mixed olefins has necessitated physical separation of the isomeric variants by other means, such as distillation, in order to isolate a product which is rich in the α-methylalkyl carboxylate.

Alkyl esters of carboxylic acids are useful as solvents, plasticizers and chemical intermediates. α-Methylalkyl carboxylates are particularly useful for making secondary alcohols with hydroxyl attachment at the 2-carbon. By utilization of the herein disclosed method, products normally derived from pure α-olefins can now be prepared from less expensive linear olefin mixtures.

SUMMARY OF THE INVENTION

It has now been discovered that certain zeolite materials may be utilized to promote reaction between olefins and carboxylic acids to produce alkyl carboxylates. In a particularly preferred embodiment, α-methylalkyl carboxylates may be prepared as the major product from the reaction of carboxylic acids and internal linear olefins, olefin mixtures or α-olefins. Specifically, the α-methylalkyl carboxylates contemplated herein are those described by the formula:

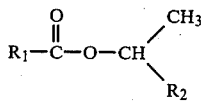

wherein:
$R_1$ = alkyl, aryl, haloalkyl or hydrogen
$R_2$ = $C_1$–$C_{20}$ alkyl, heteroalkyl or cycloalkyl The method comprises reacting a carboxylic acid having the formula

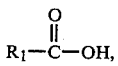

$R_1$ being described above, with an olefin having from 3 to about 20 carbon atoms. Substantially any linear, slightly branched, cyclic or heteroatom-substituted olefin may be employed, regardless of the position of the carbon-carbon double bond. However, linear olefins are preferred.

A wide range of temperature and pressure conditions are found to be conducive to the reaction, which may be successfully carried out at 25° C. to 600° C. and $10^4$Pa to $10^7$Pa (0.1 to 100 atmospheres) pressure. Temperatures of between 75° C. and 400° C. are preferred, as are pressures of $10^5$Pa to $40 \times 10^5$Pa (1 to 40 atmospheres). The reaction may be usefully carried out in either the liquor or vapor phase, although it may be found preferable to employ liquid phase reaction.

The particular type of zeolite catalysts which are found to promote this novel, selective addition reaction are characterized by their open crystal structure having channels or networks of pores which provide restricted passageways for entry and egress of the organic reactants. These zeolites may be identified by their characteristic Constraint Index of 1 to 12 and their relatively high silica to alumina ratios of at least 12. There are several known members of the class, such as zeolites ZSM-5, ZSM-11, ZSM-12, ZSM-23, ZSM-35, ZSM-38 and ZSM-48, and zeolite ZSM-12 is prefered.

DESCRIPTION OF SPECIFIC EMBODIMENTS

A one-step process has now been found for the manufacture of alkyl carboxylates from carboxylic acids and olefins, with especially desirable selectivity to α-methylalkyl carboxylates. By utilization of the particular type of zeolite catalyst described hereinafter, it now becomes possible to react carboxylic acids with olefins having the carbon-carbon double bond in substantially any position in the molecule and produce an adduct wherein the carboxylate has attached principally at the #2 carbon of the olefin molecule. This is in striking contrast to the reaction product resulting from utilization of Lewis acid and mineral acid catalysts wherein the carboxylate would attach at the carbons on either side of the double bond and, unless the site of the unsaturation included the #2 carbon atom, the resultant yield of α-methylalkyl carboxylates would comprise no more than a minor byproduct.

The carboxylic acids useful in the process of the present invention are preferably alkyl carboxylic acids having from 1 to about 10 carbon atoms therein. Included within this group are, for example, formic acid, acetic acid, propionic acid, butyric acid and hexanoic acid. Slightly branched alkyl carboxylic acids are also useful, such as, for instance, isobutyric acid. Haloalkyl carboxylic acids, such as chloroacetic acid, fluoroacetic acid and trifluoroacetic acid may be employed. Also, aryl carboxylic acids will be found desirable in some instances, including benzoic acid, para-toluic acid and para-chlorobenzoic acid.

Olefins suitable for manufacture of α-methylalkyl carboxylates as described herein are not limited to α-olefins. Rather, it has been found that substantially any olefinic hydrocarbons may be employed without regard to the location of the site of unsaturation. Mixed isomers of a given olefin are particularly desirable due to their ready availability and relatively low cost. Linear $C_3$–$C_{20}$ olefins are especially preferred, but slightly branched olefins may also be employed. Some non-limiting examples include propylene, butene, octene, dodecene, hexadecene and 1-methylnonene.

Addition of carboxylic acids to cyclic olefins may also be carried out by the present procedure. Such cyclic olefins would include, for example, cyclohexene, cyclopentene, methylcyclopentene, norbornene, and camphene.

Although hydrocarbon olefinic compounds are preferred, one may in some cases wish to utilize hetero-substituted olefins. Some illustrative examples of useful compounds would include butenyl acetate and chlorooctene.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

$$(0-15)RN : (0-1.5)M_{2/n}O : (0.2)Al_2O_3 : (100)SiO_2$$

wherein:

M is at least one cation having a valence n; and
RN is a $C_1$–$C_{20}$ organic compound having at least one amine functional group of $pK_a \geq 7$.

It is recognized that, particularly when the composition contains tetrahedral framework aluminum, a fraction of the amine functional groups may be protonated. The doubly protonated form, in conventional notation, would be $(RNH)_2O$ and is equivalent in stoichiometry to $2\,RN + H_2O$.

The characteristic X-ray diffraction pattern of the synthetic zeolite ZSM-48 has the following significant lines:

| Characteristic Lines of ZSM-48 | |
| --- | --- |
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W–S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | | BROAD | PREFERRED |
|---|---|---|---|
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH^-/SiO_2$ | = | 0 to 0.25 | 0 to 0.1 |
| $H_2O/SiO_2$ | = | 10 to 100 | 20 to 70 |
| $H^+(added)SiO_2$ | = | 0 to 0.2 | 0 to 0.05 | wherein RN is a $C_1$–$C_{20}$ organic compound having amine functional group of $pK_a \geq 7$. The mixture is maintained at 80°–250° C. until crystals of the material are formed. H+(added) is moles acid added in excess of the moles of hydroxide added. In calculating H+(added) and OH values, the term acid (H+) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pK_a \geq 7$, as defined above, and includes such compounds as $C_3$–$C_{18}$ primary, secondary, and tertiary amines, cyclic amine (such as piperidine, pyrrolidine and piperazine), and polyamines such as $NH_2$—$C_nH_{2n}$—$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 and ZSM-12 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, whigh might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, NcNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

A useful modifying treatment entails steaming of the zeolite by contact with an atmosphere containing from about 5 to about 100 percent steam at a temperature of from about 250° C. to 1000° C. Steaming may last for a period of between about 0.25 and about 100 hours and may be conducted at pressures ranging from sub-atmospheric to several hundred atmospheres to reduce the alpha value of the zeolite to less than 500, and preferably less than 20, but greater than zero.

The process of this invention is carried out such that the organic reactants, i.e., the carboxylic acid and the olefinic compound, are brought into contact with the particular type of zeolite material described herein in a suitable reaction zone. The temperature is elevated to a level conducive to the addition reaction. Suitable temperatures are from about 25° C. to about 600° C., but temperatures of between 75° C. and 400° C. are preferred. The reaction zone will preferably be pressurized to approximately $10^5$Pa to $40 \times 10^5$Pa (1 to 40 atmospheres) pressure, but pressures falling within the range of $10^4$Pa to $10^7$Pa (0.1 to 100 atmospheres) will be found to be utilizable.

The alkylation process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The following examples are provided to illustrate the process of this invention and to aid those in the art in the understanding thereof, but clearly should not be taken as presenting undue limitations thereon:

EXAMPLE 1

One gram of HZSM-:12 zeolite ($SiO_2/Al_2O_3$ mole ratio 70) was placed in a 300 cc stainless steel autoclave equipped with a magnetically driven stirrer. The catalyst had been ground to a powder and calcined prior to use. Added 100 ml of a mixture of acetic acid and 1-octene (molar ratio=4/1) and heated to temperature. Samples were withdrawn periodically through a dip tube and analyzed. Results are summarized in TABLE I.

TABLE I

| REACTION OF 1-OCTENE AND ACETIC ACID OVER HZSM—12 | | | | | | |
| --- | --- | --- | --- | --- | --- | --- |
| Reaction Time | Temperature | Pressure | Yield of $C_8OAc$ | $C_{18}H_{17}OAc$ Isomer Distribution | | |
| | | | | 2 | 3 | 4 |
| 3.5 hr | 150° C. | 160 psig | 5.9 wt % | 96.9% | 2.9% | 0.2% |
| 5.6 hr | 200° C. | 240 psig | 23.9 wt % | 94.1% | 5.5% | 0.4% |

TABLE I-continued

REACTION OF 1-OCTENE AND ACETIC ACID OVER HZSM—12

| Reaction Time | Temperature | Pressure | Yield of C₈OAc | $C_{18}H_{17}OAc$ Isomer Distribution | | |
|---|---|---|---|---|---|---|
| | | | | 2 | 3 | 4 |
| 73.2 hr | 200° C. | 230 psig | 32.2 wt % | 91.4% | 8.1% | 0.5% |

The 1-octene and acetic acid have been converted to primarily 2-octyl acetate. The 3- and 4-octyl acetates were produced as minor byproducts and no 1-octyl acetate was formed.

EXAMPLE 2

2-Octene and acetic acid were reacted in the same manner as in Example 1. The catalyst was another sample of the same HZSM-12 zeolite and the 2-octene reactant was a mixture of the cis and trans isomers. The results are shown in TABLE II.

TABLE II

REACTION OF 2-OCTENE AND ACETIC ACID OVER HZSM—12

| Reaction Time | Temperature | Pressure | Yield of C₈OAc | $C_8H_{17}OAc$ Isomer Distribution | | |
|---|---|---|---|---|---|---|
| | | | | 2 | 3 | 4 |
| 0.8 hr | 150° C. | 175 psig | 0.4 wt % | 77% | 23% | — |
| 1.4 hr | 200° C. | 245 psig | 6.9 wt % | 79% | 19% | 1.7% |
| 2.3 hr | 200° C. | 245 psig | 12.9 wt % | 79% | 20% | 0.6% |
| 3.3 hr | 200° C. | 235 psig | 18.3 wt % | 78% | 22% | 0.7% |
| 4.3 hr | 225° C. | 300 psig | 22.0 wt % | 75% | 24% | 1.0% |
| 6.3 hr | 225° C. | 300 psig | 24.1 wt % | 69% | 28% | 2.2% |

The use of HZSM-12 zeolite to promote the reaction is seen to significantly alter the isomeric product distribution from that which would normally be expected. Using the same reactor system and procedure, comparative runs were made with other catalysts as follows:

EXAMPLE 3

2 Octene and acetic acid were reacted over 1.0 g of HZSM-5 zeolite. The conditions of reaction were the same as in Example 2 and the results are summarized in TABLE III.

TABLE III

REACTION OF 2-OCTENE AND ACETIC ACID OVER HZSM-5

| Reaction Time | Temperature | Pressure | Yield of C₈OAc | $C_8H_{17}OAc$ Isomer Distribution | | |
|---|---|---|---|---|---|---|
| | | | | 2 | 3 | 4 |
| 2.0 hr | 200° C. | 290 psig | 3.6 wt % | 80% | 17% | 3% |
| 2.8 hr | 250° C. | 460 psig | 9.0 wt % | 70% | 23% | 7% |
| 4.0 hr | 250° C. | 445 psig | 10.4 wt % | 55% | 30% | 16% |
| 6.1 hr | 250° C. | 440 psig | 13.0 wt % | 46% | 32% | 23% |

EXAMPLE 4

Amorphous silica-alumina: $SiO_2/Al_2O_3 = 90/10$.

EXAMPLE 5

Zeolite REY.

EXAMPLE 6

A Lewis Acid catalyst: $BF_3.Et_2O$.

A mixture of acetic acid and 2-octene (molar ratio 4:1, respectively) was mixed with a small amount of boron trifluoride etherate catalyst and the mixture heated to 90° C. on a steam bath. Samples were removed and analyzed at 1.2 and 2.7 hours.

The reactions of Examples 4–6 are summarized in TABLE IV and a comparison with the HZSM-5 and HZSM-12 zeolite is presented in TABLE V.

TABLE IV

REACTION OF 2-OCTENE AND ACETIC ACID

| Reaction Time | Temperature | Pressure | Yield of C₈OAc | $C_8H_{17}OAc$ Isomer Distribution | | |
|---|---|---|---|---|---|---|
| | | | | 2 | 3 | 4 |
| Catalyst: | $BF_3.Et_2O$ | | | | | |
| 1.2 hr | 90° C. | 0 psig | 37.3 wt % | 52% | 45% | 3% |
| 2.7 hr | 90° C. | 0 psig | 57.0 wt % | 52% | 44% | 4% |
| Catalyst: | amorphous $SiO_2/Al_2O_3$ | | | | | |
| 0.6 hr | 250° C. | 400 psig | 5.0 wt % | 58% | 37% | 5% |
| 1.8 hr | 250° C. | 400 psig | 11.1 wt % | 59% | 36% | 5% |
| 17.5 hr | 250° C. | 400 psig | 17.4 wt % | 62% | 30% | 8% |
| Catalyst: | REY | | | | | |
| 2.2 hr | 200° C. | 215 psig | 1.9 wt % | 59% | 37% | 4% |
| 3.2 hr | 250° C. | 380 psig | 9.5 wt % | 60% | 35% | 5% |
| 3.9 hr | 250° C. | 380 psig | 14.5 wt % | 59% | 34% | 6% |
| 5.0 hr | 250° C. | 375 psig | 16.6 wt % | 59% | 31% | 10% |

TABLE V

CATALYST COMPARISONS

| Catalyst | 2-C₈OAc | 3-C₈OAc | 4-C₈OAc | Ratio: $\frac{2C_8OAc}{3 + 4 - C_8OAc}$ |
|---|---|---|---|---|
| HZSM-5 | 80% | 17% | 3% | 4.0 |
| HZSM-12 | 79% | 20% | 0.6% | 3.4 |
| $BF_3.Et_2O$ | 52% | 44% | 4% | 1.1 |
| $SiO_2/Al_2O_3$ | 62% | 30% | 8% | 1.6 |
| REY | 60% | 35% | 5% | 1.5 |

It will be clearly seen from the data that the proportion of 2-isomer produced is significantly improved by utilization of HZSM-5 and HZSM-12 zeolites to catalyze the reaction. Similar improvement can be expected from the other zeolites encompassed within the herein described class.

EXAMPLE 7

To demonstrate even more dramatically the novel selectivity of the herein disclosed process, an olefin having the double bond in a more internal location—i.e., trans-4-octene—was reacted with acetic acid in the presence of HZSM-12. The reaction mixture contained a 10/1 molar ratio of HOAc to trans-4-octene. The results are given in TABLE VI.

TABLE VI

REACTION OF 4-OCTENE AND ACETIC ACID OVER HZSM-12

| Reaction Time | Temperature | Pressure | Yield of C₈OAc | $C_8H_{17}OAc$ Isomer Distribution | | |
|---|---|---|---|---|---|---|
| | | | | 2 | 3 | 4 |
| 1.3 hr | 150° C. | 170 psig | 1.5 wt % | 61% | 24% | 15% |
| 2.1 hr | 200° C. | 225 psig | 10.5 wt % | 60% | 30% | 10% |
| 2.8 hr | 200° C. | 225 psig | 17.3 wt % | 58% | 32% | 10% |
| 3.6 hr | 200° C. | 225 psig | 24.3 wt % | 57% | 32% | 11% |
| 5.6 hr | 200° C. | 225 psig | 27.4 wt % | 54% | 33% | 12% |

EXAMPLES 8–10

Using the same reaction mixture as Example 7, comparative reactions were carried out with a Lewis acid catalyst ($BF_3.Et_2O$) as well with amorphous silica-alumina and zeolite REY. Results are shown in TABLE VII. A direct comparison of the isomeric distribution of the octyl acetate product with that resulting from ZSM-12 is provided in TABLE VIII.

TABLE VII
REACTION OF 4-OCTENE AND ACETIC ACID

| Reaction Time | Temperature | Pressure | Yield of $C_8OAc$ | $C_8H_{17}OAc$ Isomer Distribution 2 | 3 | 4 |
|---|---|---|---|---|---|---|
| Catalyst: | | | $BF_3 \cdot Et_2O$ | | | |
| hr | 90° C. | 0 psig | 9.0 wt % | 1% | 5% | 94% |
| 4.3 hr | 90° C. | 0 psig | 65.7 wt % | 8% | 18% | 75% |
| Catalyst: | amorphous $SiO_2/Al_2O_3$ | | | | | |
| 2.3 hr | 250° C. | 390 psig | 3.5 wt % | 5% | 10% | 85% |
| 3.5 hr | 250° C. | 390 psig | 6.9 wt % | 5% | 10% | 85% |
| 4.9 hr | 250° C. | 390 psig | 8.4 wt % | 6% | 11% | 83% |
| Catalyst: | REY | | | | | |
| 1.6 hr | 200° C. | 225 psig | 4.1 wt % | 4% | 7% | 89% |
| 2.1 hr | 250° C. | 375 psig | 7.1 wt % | 4% | 10% | 86% |
| 3.6 hr | 250° C. | 390 psig | 11.5 wt % | 10% | 17% | 73% |

TABLE VIII
CATALYST COMPARISONS

| Catalyst | 2-$C_8OAc$ | 3-$C_8OAc$ | 4-$C_8OAc$ | Ratio: $\frac{2C_8OAc}{3 + 4 - C_8OAc}$ |
|---|---|---|---|---|
| HZSM-12 | 60% | 30% | 10% | 1.50 |
| $BF_3 \cdot Et_2O$ | 8% | 18% | 75% | 0.09 |
| $SiO_2/Al_2O_3$ | 6% | 11% | 83% | 0.06 |
| REY | 10% | 17% | 73% | 0.11 |

As the comparisons of TABLE VIII show, conventional catalysts and the large pore zeolite, REY, all give rise to the product arising from addition of the carboxylic acid to the double bond. HZSM-12, however, selectively yields 2-octyl acetate as the major product.

EXAMPLE 11

A mixed octene sample was utilized to demonstrate the unique selectivity of the process with an isomeric mixture of olefins. The octene consisted of 25% 1-octene, 25% t-2-octene, 25% t-3-octene and 25% t-4-octene. Using the same autoclave procedure as above, acetic acid and the mixed octenes (in a molar ratio of 8:1) were reacted over HZSM-12 zeolite. The results are shown in TABLE IX.

TABLE IX
REACTION OF MIXED OCTENES AND ACETIC ACID OVER HZSM-12

| Reaction Time | Temperature | Pressure | Yield of $C_8OAc$ | $C_8H_{17}OAc$ Isomer Distribution 2 | 3 | 4 |
|---|---|---|---|---|---|---|
| 0.5 hr | 150° C. | 155 psig | 10.5 wt % | 88% | 11% | 1% |
| 1.75 hr | 150° C. | 140 psig | 14.1 wt % | 86% | 13% | 1% |
| 2.75 hr | 150° C. | 140 psig | 17.0 wt % | 86% | 13% | 1% |
| 3.7 hr | 200° C. | 185 psig | 22.5 wt % | 78% | 20% | 2% |

Assuming an equal probability of addition of the acid to both ends of the double bond (except no addition to the terminal position), one would normally expect an octylacetate isomer distribution of 37.5% 2-isomer, 25% 3-isomer and 37.5% 4-isomer. The actual result, utilizing the process of this invention, indicates a very high level of selectivity to the desired 2-isomer.

EXAMPLE 12

Using the same reaction method, 4-octene and propionic acid were reacted over 1.0 g of HZSM-12. The reaction mixture consisted of 100 ml of an 8:1 molar ratio mixture of the acid to the olefin. The results are shown in TABLE X.

TABLE X
REACTION OF 4-OCTENE AND PROPIONIC ACID OVER HZSM-12

| Reaction Time | Temperature | Pressure | $C_8H_{17}OAc$ Isomer Distribution 2 | 3 | 4 |
|---|---|---|---|---|---|
| 1.0 hr | 150° C. | 150 psig | 62% | 16% | 22% |
| 2.4 hr | 200° C. | 195 psig | 59% | 21% | 20% |

EXAMPLE 13

Isobutyric acid and t-4-octene (molar ratio=6.2:1) were reacted over HZSM-12 zeolite. The results are summarized below.

TABLE XI
REACTION OF 4-OCTENE AND ISOBUTYRIC ACID OVER HZSM-12

| Reaction Time | Temperature | Pressure | Yield of $C_8OBu$ | $C_8H_{17}OBu$ Isomer Distribution 2 | 3 | 4 |
|---|---|---|---|---|---|---|
| 3.1 hr | 200° C. | 200 psig | 3.8 wt % | 67% | 21% | 12% |
| 4.0 hr | 250° C. | 275 psig | 7.0 wt % | 50% | 32% | 18% |

EXAMPLE 14

To illustrate reaction of a cycloolefin in the process, a mixture of norbornene (bicyclo [2.2.1]-2-heptene) and acetic acid was reacted over HZSM-12 zeolite. The reaction was carried out on a steam bath at about 100° C. for 5.5 hours. The addition product, norbornyl acetate, was formed in about 95% yield.

EXAMPLE 15

Propylene was reacted with acetic acid in the presence of HZSM-12. Into a 300 cc autoclave were placed 70 ml of glacial acetic acid and 1.0 g of the HZSM-12 zeolite. The reactor was heated to 200° C. and liquid propylene was added at the rate of 10 ml per hour. Samples were periodically withdrawn and analyzed. The results are summarized in TABLE XII. As will be seen from the table, isopropyl acetate was formed in high yield with high purity.

TABLE XII
REACTION OF PROPYLENE WITH ACETIC ACID

| Reaction | Temperature | Pressure | Yield of isopropyl acetate | Yield of n-propyl acetate | Isopropyl acetate, % of theory |
|---|---|---|---|---|---|
| 0.5 hr | 200° C. | 160 psig | 2.9 wt % | — | 36% |
| 1.5 hr | 200° C. | 240 psig | 8.0 wt % | — | 34% |
| 2.5 hr | 200° C. | 340 psig | 12.8 wt % | — | 36% |
| 3.5 hr | 200° C. | 450 psig | 17.0 wt % | — | 36% |
| 4.5 hr | 200° C. | 550 psig | 20.5 wt % | — | 35% |
| 20.9 hr | 200° C. | 400 psig | 31.6 wt % | 0.03 wt % | 50% |

EXAMPLE 16

Ethylene and acetic acid were reacted in the presence of HZSM-12 in a manner similar to that employed in Example 15. The autoclave, containing 1.0 g of HZSM-12 and 70 ml of glacial acetic acid, was heated to 200° C. and then pressurized to 500 psig with ethylene. At 2.5 hours, the temperature was raised to 250° C. and at 4.0 hours more ethylene was added to a pressure of 1000 psig. The level of reaction was low, but ethyl acetate was produced as the major reaction product.

Having thus described the present invention with the aid of certain specific examples thereof, it is to be understood that such examples are intended to be merely illustrative of the disclosed process. Many variations thereon may be made without departing from the spirit of the disclosed invention, as will be evident to those skilled in the art, and such variations are intended to come within the scope of the following claims:

I claim:

1. A method for the preparation of an alkyl carboxylate reaction product containing α-methylalkyl carboxylates as the major alkyl carboxylate product, said method comprising:

reacting a carboxylic acid having the formula

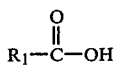

wherein $R_1$ is alkyl, aryl, haloalkyl or hydrogen; with a linear or slightly branched olefinic compound having up to about 20 carbon atoms therein, and said olefinic compound further having no unsaturation at the site of the #2 carbon atom;

said reaction being carried out at a temperature of between about 250° C. and 600° C., a pressure of within the approximate range of $10^4$Pa to $10^7$Pa, and in the presence of a crystalline zeolite catalyst characterized by a silica to alumina mole ratio of at least 12 and a Constraint Index of within the range of 1 to 12.

2. The method of claim 1 wherein said temperature is between 75° C. and 400° C.

3. The method of claim 1 wherein said pressure is between $10^5$Pa and $4 \times 10^6$Pa.

4. The method of claim 1 wherein said carboxylic acid has from 1 to about 10 carbon atoms therein.

5. The method of claim 4 wherein said carboxylic acid is chosen from the group consisting of acetic acid, propionic acid and butyric acid.

6. The method of claim 1 wherein said olefinic compound is a linear olefin.

7. The method of claim 1, 2, 3, 4, 5 or 6 wherein said zeolite is chosen from the group consisting of ZSM-5, ZSM-11, ZSM-12, ZSM-23, ZSM-35, ZSM-38 and ZSM-48.

8. The method of claim 7 wherein said zeolite is ZSM-5.

9. The method of claim 8 wherein said ZSM-5 additionally comprises a binder therefor.

10. The method of claim 7 wherein said zeolite is ZSM-12.

11. The method of claim 10 wherein said ZSM-12 additionally comprises a binder therefor.

12. The method of claim 1 wherein said zeolite additionally comprises a binder therefor.

* * * * *

UNITED STATES PATENT OFFICE
CERTIFICATE OF CORRECTION

Patent No. 4,365,084                     Dated December 21, 1982

Inventor(s) Lewis Brewster YOUNG

It is certified that error appears in the above-identified patent and that said Letters Patent are hereby corrected as shown below:

Column 9, Line 1, "whigh" should be -- which --.

Column 10, Line 51, "HZSM-:12" should be -- HZSM-12 --.

Column 13, Line 9, "$BF_3 \cdot Et_2O$" should be under the "Temperature" column instead of the "Yield" column.

Column 13, Line 10, -- 0.6 -- should be inserted before "hr".

Column 15, Line 27, in Claim 1, "250°C" should be -- 25°C --.

Signed and Sealed this

Thirty-first Day of May 1983

[SEAL]

Attest:

DONALD J. QUIGG

Attesting Officer      Acting Commissioner of Patents and Trademarks